United States Patent [19]

Braswell et al.

[11] Patent Number: 6,096,307

[45] Date of Patent: Aug. 1, 2000

[54] **COMPOSITIONS FOR IMMUNOSTIMULATION CONTAINING *ECHINACEA ANGUSTOFOLIA*, BROMELAIN, AND LYSOZYME**

[75] Inventors: A. Glenn Braswell, Suite 420, 520 Washington Blvd., Marina Del Rey, Calif. 90292; Aftab J. Ahmed, Marina Del Rey, Calif.

[73] Assignee: A. Glenn Braswell, Atlanta, Ga.

[21] Appl. No.: 08/988,846

[22] Filed: Dec. 11, 1997

Related U.S. Application Data

[60] Provisional application No. 60/032,394, Dec. 11, 1996.

[51] Int. Cl.[7] .......................... A61K 38/43; A61K 38/54; A61K 38/46; A61K 35/78; A61K 38/47
[52] U.S. Cl. .................. 424/94.1; 424/94.2; 424/94.61; 424/94.65; 424/195.1; 514/885
[58] Field of Search ............................ 424/195.1, 94.1, 424/94.2, 94.61, 94.65; 514/885

[56] References Cited

U.S. PATENT DOCUMENTS

| | | | |
|---|---|---|---|
| 4,388,331 | 6/1983 | Miller | 426/63 |
| 4,857,512 | 8/1989 | Wagner et al. | 514/54 |
| 5,326,858 | 7/1994 | Lichenstein et al. | 536/23.2 |

FOREIGN PATENT DOCUMENTS

| | | |
|---|---|---|
| 32 17 214 A1 | 11/1983 | Germany . |
| 37 44 345 A1 | 7/1989 | Germany . |
| 55-43040 | 3/1980 | Japan . |
| WO 90/01947 | 3/1990 | WIPO . |
| WO 90/01948 | 3/1990 | WIPO . |
| 9615682 | 5/1996 | WIPO . |

OTHER PUBLICATIONS

Remington's Pharmaceutical Sciences, 16th Edition, Mack Publishing Co., Easton, PA, pp. 1553–1557, 1980.

J. Drews, "Possibilities of Immunostimulation," Swiss Forma, 2, 9 (49) (1980).

Murray, "The Healing Power of Herbs", The Enlightened Person's Guide to the Wonders of Medicinal Plants, 1995, 2nd Edition, pp. 92–107.

Murray, "Echinacea: Pharmacology And Clinical Applications", The American Journal of Natural Medicine, vol. 2, No. 1, Jan./Feb. 1995, pp. 18–24.

M. Heidelberger, "Cross–Reactions of Plant Polysaccharides in antipneumococcal and Other Antisera, an Update", Fortschritte d. Chem. Org. Naturst., 1982, pp. 287–298.

Derwent English–language Abstract for DE 37 44 345 A1.
Derwent English–language Abstract for DE 32 17 214 A1.

*Primary Examiner*—Jon P. Weber
*Assistant Examiner*—Janet M. Kerr
*Attorney, Agent, or Firm*—Don J. Pelto; Lawrence M. Sung; Jeff E. Schwartz

[57] ABSTRACT

A composition for immunostimulation contains an effective amount of an Echinacea extract, Bromelain and Lysozyme. In particular, a treatment for excessive bacterial growth in the oral cavity includes administration of such a composition.

16 Claims, No Drawings

COMPOSITIONS FOR IMMUNOSTIMULATION CONTAINING *ECHINACEA ANGUSTOFOLIA*, BROMELAIN, AND LYSOZYME

This application claims the benefit of U.S. provisional application No. 60/032,394, filed Dec. 11, 1996.

BACKGROUND OF THE INVENTION

1. Field of the Invention

The present invention relates to a composition for immunostimulation used for the treatment of at least bacterial growth, which may be administered orally.

2. Description of the Related Art

Immunostimulation as a therapeutical concept has long been known in medicine. In general, it is defined as the injection of substances that themselves have only weak, if any, antigenic effect, but are nevertheless able to induce the body's own defense mechanisms in a nonspecific or specific manner. A great number of substances are known to be able to stimulate immune defense, especially various minerals such as $Al(OH)_3$, $MgSO_4$, beryllium, vegetable oils with or without added mycobacteria, and a number of constituents of plants. The entire complex subject of immunostimulation was described in detail, for example, by L. Chudid, et al. in *Immunstimulation*, Springer Verlag, Heidelberg, N.Y., 1980; M. Heidelberger, "Structure and Immunological Specificity of Polysaccharides," *Fortschritte d. Chem. Org. Naturst.*, Vol. 42, p. 288 (1982); and J. Drews, "Possibilities of Immunostimulation," Swiss Forma, 2, 9 (49) (1980).

In most known cases, it is impossible to define the exact mode of action of the immunostimulating substances. These substances are known to generally influence the proliferation of the immunocompetent cells. The primary targets of the action of immunostimulating substances are known to be macrophages and granulocytes, as well as T and B lymphocytes.

The effect of the immunostimulants may be direct or indirect, for example, via the complement system or the lymphocytes, via the production of interferon or lysozymal enzymes (e.g. lymphokines, colony-stimulating factor, and others), as well as via an increase in macrophagocytosis and microphagocytosis. Cascade effects and simultaneous influences on a plurality of defense mechanisms are expected because of the mix of nonspecific and specific defense mechanisms.

Medicinal applications of immunostimulation are primarily for the therapy of mixed infections and chronic, persistent, chemotherapy-resistant bacterial and viral infections. Immunostimulants may also be used to prevent opportunistic infection of patients at risk, for therapy of malignant diseases, and for treatment of autoimmune diseases. Generally, immunostimulants have been used in combination with known anti-bacterial or anti-viral substances, such as antibiotics. However, the use of antibiotics and other such substances is known to decrease in effectiveness over time. It is also well known that viral and bacterial strains tend to develop that are resistant to such measures.

However, the use of immunostimulants has not been shown to have similar effects. In other words, immunostimulants do not cause the development of more virulent strains of bacterial or viral infections. Therefore, the use of immunostimulants, alone or in combination with other measures, is increasing.

SUMMARY OF THE INVENTION

The present invention is directed to a composition that enhances the immune system. In particular, the composition causes immunostimulation, providing at least anti-bacterial effects in the area of immediate use.

One embodiment of this invention is directed to a composition for oral administration for the control and prevention of bacterial growth on the tongue and in the mouth, which may cause, for example, halitosis or gum disease, respectively.

DETAILED DESCRIPTION OF PREFERRED EMBODIMENTS

According to the present invention, a composition containing an Echinacea extract, Bromelain and Lysozyme may be administered orally to control bacterial growth, at least in the mouth and on the tongue. The composition may be administered orally by any known means of oral administration, but preferably in the form of a lozenge or tablet.

The composition combines the effect of three agents known to cause immunostimulation. Acting together, the agents have a synergistic effect, thereby greatly increasing the reaction of the immune system of the subject taking the composition. The composition may be used to reduce or prevent bacterial growth, viral infection, or tumor growth, as well as providing anti-inflammatory effects at least in the area of administration.

Each component of the composition is known to have certain immunostimulant effects on the human immune system.

Echinacea extracts, particularly Echinacea Angustofolia, are known to stimulate the production of granulocytes, macrophages, leukocytes and lymphocytes. They are also known to inhibit both viral and bacterial activity.

Over 350 studies have been done on the Echinacea species and its various varieties. Extracts of both the aerial and root portions of the plants have been used. The studies have demonstrated that Echinacea extracts promote tissue regeneration; reduce inflammation; inhibit the enzyme hyaluronidase; stimulate cell, and particularly fibroblast, production; and enhance secretion of adrenal cortex hormones. In this manner, Echinacea extracts activate alternative complement pathways, thereby elevating low serum white blood cell counts and activating white blood cells by bonding to their receptor sites. Cell mediated immunity is achieved through promotion of nonspecific T-cell activation, and increases in production of interferon and other immune potentiators. This cell mediated immunity is important in the resistance of mold-like bacteria, yeast, fungi, parasites and viruses.

The anti-bacterial activity of Echinacea extracts is generally considered to be weak. However, some anti-bacterial activity has been shown in relation to Staphylococcus aureus, Corynebacterium diphtheria and Proteus vulgaris. It is known that 6.3 milligrams of an Echinacea extract is equivalent to 10 Oxford units of penicillin.

The anti-viral effects of Echinacea include action against influenza, herpes and vesicular stomatitis. It is believed that Echinacea blocks virus receptors on the cell surface as well as inhibiting hyaluronidase.

Further, through general activation of the immunological system, it is believed that Echinacea may also provide some effects against tumors. Certain extracts of Echinacea root have shown direct anti-cancer activity in vivo.

Echinacea is nonmutagenic and nontoxic. The only known side effect is an occasional slight rise in temperature (0.5–1.0 ° F.) upon intravenous administration.

Lysozyme is another natural substance with known immunological effects. It is a natural polypeptide of 129 amino acids. It is known to provide anti-bacterial and anti-viral actions by modulating the immune response system.

Lysozyme activates the immune response system, increasing the bactericidal capacity of the antibody complement system. Lysozyme is frequently added to infant formulas to prevent gastroenteritis and to reduce allergic reactions. Lysozyme is currently used in Europe and Japan in over-the-counter cold remedies.

Lysozyme acts by lytic activity on bacterial walls. In particular, a regulatory effect is observed on the intestinal bacterial ecosystem.

Lysozyme also possesses anti-viral activity, activating defense factors and/or interacting with surface cell receptors, thereby inhibiting syncytiogenetic activity.

The immune response modulating effect of Lysozyme is attributed to regulation of the complementary activity, interference with reproduction and differentiation of immunocompetent cells, intervention in phagocytosis, and an increase in bactericidal capacity of the antibody complement system.

As with Echinacea, Lysozyme has proven to have negligible, if any, toxicity and is nonmutagenic. Therefore, it is considered to be a safe compound for medicinal administration.

Bromelain is a natural extract of pineapples. Bromelain has been shown to have a potentiating effect on antibody activity and is known to be synergistic with Lysozyme. Bromelain also has a potentiating effect on serum levels of a variety of antibiotics. Further, Bromelain has been shown to have a strong Interleukin-2 (IL-2) like activity, stimulating, human natural killer cells against melanoma cells in vitro. Bromelain has shown a synergistic effect with IL-2. Bromelain is also known to stimulate human blood lymphocytes to secrete tumor nucrosis factor-alpha (TNF-$\alpha$) and IL-2, thereby activating natural immune cells that are capable of attacking and killing tumor cells. Therefore, it is believed that Bromelain is a highly active immunomodulator that may augment anti-tumor defense processes in the body.

Bromelain can be used in conjunction with antibiotics, forming synergistic compositions.

It has now been discovered that, according to the present invention, the use of an Echinacea extract, particularly Echinacea Angustofolia, Bromelain and Lysozyme in combination results in enhanced or synergistic immunostimulation of the body's immune system. The use of all three agents in combination provides a combination of anti-bacterial, anti-viral and, possibly, anti-tumor activity. Further, other effects, such as the anti-inflammatory effect of Echinacea, are also realized.

Therefore, the composition of this invention provides an improved method of both curing and preventing bacterial and viral infections. Particularly when administered orally, the composition provides a superior means of both curing and preventing excess bacterial growth in the mouth and on the tongue, which cause, for example, gum disease and halitosis, respectively.

The composition of the present invention is comprised of an effective amount of each component. The composition may be formulated as any acceptable means of administration. In particular, the composition may be administered orally by means such as lozenges or tablets, the formation of which is well known to those in the art. Other pharmaceutical compositions such as solutions, sprays and drops may also be used.

In particular, the agents should be present in an effective amount. The Echinacea extract is preferably standardized to include from 4–7% Echinacosides, more preferably about 6%, per milligram Echinacea extract, and may be present in an amount of from about 1.5–4.0% by weight of the composition. Bromelain preferably has an activity of about 750–1200 GDU/g, more preferably about 1000 GDU/g, and should be present in an amount of from about 0.5–1.0% by weight of the composition. Lysozyme preferably has an activity of about 15,000–30,000 Shugar units/mg, more preferably about 20,000–25,000 Shugar units/mg, and is preferably present in an amount of from about 0.25–0.70% by weight of the composition. The most preferred amounts of these agents is: Echinacea, 2.5% by weight; Bromelain, 0.65% by weight; and Lysozyme, 0.40% by weight. However, amounts outside of these ranges are possible and may be preferable in some embodiments.

Formulations for oral administration may also include known flavorants such as natural fruit or mint flavors, as well as sweeteners, such as Sorbital™, colorants, fillers, carriers, excipients and the like.

Further, the composition may include citric acid, or other like substances, to accelerate the process of bacterial degradation.

The composition may be administered preventively, in which case the dosage may be 2 to 3 tablets daily. Upon onset of an affliction, such as halitosis or gum disease, dosage may be increased depending on personal needs. The composition, when taken orally, may cause a short term tingling effect in the mouth during use.

The recommended dosage will, of course, vary depending on such factors as the relative units of each agent in the composition, the means of administration, and the age, sex and weight of the patient. Manipulation of the dosage and strength will be apparent to one of ordinary skill in the art based on the present disclosure.

The following is an example of a composition for oral administration, according to one embodiment of the present invention.

EXAMPLE

A chewable tablet is formed by means well known in the art containing the following:

| | |
|---|---|
| *Echinacea Angustofolia* (7:1; min. 4% echinacosides) | 30 mg |
| Bromelain (1,000 GDU/g) | 8 mg |
| Lysozyme (min. 20,000 Shugar units/mg) | 5 mg |
| Natural Orange Flavor | |
| Citric Acid | |
| Sorbital ™ | |

Dosage is 2–3 tablets daily as a preventative. Upon onset of symptoms, the dosage may be increased as needed.

What is claimed is:

1. A composition for immunostimulation comprising about 1.5 to 4.0% by weight of the total composition of an extract of Echinacea Angustofolia, about 0.5 to 1.0% by weight of the total composition of bromelain having an activity of from about 750 to 1200 GDU/g and about 0.25 to 0.70% by weight of the total composition of lysozyme having an activity of from about 15,000 to 30,000 Shugar units/mg.

2. The composition of claim 1, wherein the Echinacea extract is present in an amount of about 2.5% by weight of the total composition.

3. The composition of claim 1, wherein said bromelain activity is about 1000 GDU/g.

4. The composition of claim 1, wherein said lysozyme activity is from about 20,000–25,000 Shugar units/mg.

5. The composition of claim 1, wherein bromelain is present in an amount of about 0.65% by weight of the total composition.

6. The composition of claim 1, wherein lysozyme is present in an amount of about 0.40% by weight of the total composition.

7. The composition of claim 1, further comprising a flavorant.

8. The composition of claim 1, further comprising a sweetener.

9. The composition of claim 1, further comprising citric acid.

10. The composition of claim 1, in a formulation for oral administration.

11. The composition of claim 10, wherein the formulation is a lozenge or tablet.

12. A method of inhibiting bacterial growth, viral growth, or a combination thereof, comprising administering to a mammal in need thereof an effective amount of the composition of claim 1.

13. The method of claim 12, wherein the method is for inhibiting bacterial growth, wherein the bacterial growth is in the oral cavity, and the composition is administered in lozenge or tablet form.

14. The method of claim 12, wherein the mammal is a human.

15. A method for immunostimulation comprising administering to a mammal in need thereof an immunostimulating effective amount of the composition of claim 1.

16. The method of claim 15, wherein the mammal is a human.

* * * * *